United States Patent [19]

Dinh et al.

[11] Patent Number: 5,247,112
[45] Date of Patent: Sep. 21, 1993

[54] METHOD FOR PURIFYING SILYL KETENE ACETALS

[75] Inventors: Paul C. Dinh; Peter Y. K. Lo, both of Midland, Mich.

[73] Assignee: Dow Corning Corporation, Midland, Mich.

[21] Appl. No.: 14,927

[22] Filed: Feb. 8, 1993

[51] Int. Cl.$^5$ .............................. C07F 7/08; C07F 7/18
[52] U.S. Cl. ..................................... 556/443; 556/446; 556/448
[58] Field of Search ........................ 556/443, 446, 448

[56] References Cited

U.S. PATENT DOCUMENTS 4,746,750  5/1988  Revis .................................. 556/443
4,824,981  4/1989  Schulz et al. ...................... 556/443

FOREIGN PATENT DOCUMENTS 219322  4/1987  European Pat. Off. .

OTHER PUBLICATIONS

Ojima et al., J. Organomet. Chem. 111:43–60 (1976) "Hydrosilylation of $\alpha\beta$-unsaturated Nitriles and Esters catalyzed by tris(triphenylphosphine) chlororhodium".
Howe et al., J. Organomet. Chem. 208:401–406 (1981) "Rhodium(II) Complexes as Hydrosilylation and Hydrogenation Catalysts".

Primary Examiner—Paul F. Shaver
Attorney, Agent, or Firm—William F. Boley

[57] ABSTRACT

The present invention is a method for separating silyl ketene acetals from carbonyl by-products having a terminal olefinic bond and a boiling point similar to that of the silyl ketene acetals. The method employs a platinum catalyst which specifically effects hydrosilation of the carbonyl by-product's terminal olefinic bond by an organohydrosilane. The platinum catalyst is the reaction product of hexachloroplatinic acid and sym-tetramethyldivinyldisiloxane. In a preferred method the silyl ketene acetal is separated from the hydrosilated carbonyl by-product by distillation.

15 Claims, No Drawings

METHOD FOR PURIFYING SILYL KETENE ACETALS

BACKGROUND OF INVENTION

The present invention is a method for separating silyl ketene acetals from carbonyl by-products having a terminal olefinic bond and a boiling point similar to that of the silyl ketene acetals. The method employs a platinum catalyst which specifically effects hydrosilation of the carbonyl by-product's terminal olefinic bond by an organohydrosilane. The platinum catalyst is the reaction product of hexachloroplatinic acid and sym-tetramethyldivinyldisiloxane. In a preferred method the silyl ketene acetal is separated from the hydrosilated carbonyl by-product by distillation.

Silyl ketene acetals are useful reactive intermediates for use as coatings and bonding agents. Processes are known for the production of silyl ketene acetals, but these processes often result in the formation of undesirable carbonyl by-products having a terminal olefinic bond and a boiling point similar to that of the silyl ketene acetal. This similarity of boiling points makes it difficult to separate the silyl ketene acetals from the carbonyl by-product. Therefore, the present invention is a method for specifically hydrosilating the terminal olefinic bond of the carbonyl by-product to increase the molecular weight of the carbonyl by-product and thus facilitate its separation from the desired silyl ketene acetal. The inventors have found that a platinum catalyst which is the reaction product of hexachloroplatinic acid and sym-tetramethyldivinyldisiloxane can effect hydrosilation of the terminal olefinic bond of the carbonyl by-product without effecting hydrosilation of the desired silyl ketene acetal.

Ojima et al., J. Organometallic Chem. 111:43-60 (1976), describe a process for preparing silyl ketene acetals using tris(triphenylphosphine)chlororhodium as a catalyst for the hydrosilation of several methyl 2-alkenoates with trialkylsilanes. Ojima et al. observed in addition to the silyl ketene acetals minor quantities of a 1,2-adduct.

Howe et al., J. Organometallic Chem. 208:401-406 (1981), describe two phosphine-rhodium(II) complexes found to be active catalyst for the hydrosilation of olefins including an α,β-unsaturated ester to form a silyl ketene acetal. The phosphine-rhodium(II) complexes are bis(tris-o-tolylphosphine)dichlororhodium(II) and bis-(tricyclohexylphosphine)dichlororhodium(II).

Revis et al, EPO-219,322, Pub. Apr. 22, 1987, disclose a process for the manufacture of silyl ketene acetals, the process comprising the contacting of methacrylic acid or an ester of methacrylate acid with a hydrogen-containing silicon material in the presence of a catalyst comprising rhodium complexed with inorganic ligands. Revis et al. teach that carbonyl adducts which boil very close to the desired silyl ketene acetal can be reacted with an excess of the hydrogen-containing silicon material to form a higher boiling specie. The present process using a platinum catalyst can provide a faster and more complete conversion of the carbonyl adduct to a higher boiling specie than the process taught by Revis et al. In addition a lower concentration of platinum catalyst in relation to the concentration of the rhodium catalyst taught by Revis et al., is required.

Dinh et al., Co-Pending U.S. Pat. application No. 07/912,433, describe a process for preparing silyl ketene acetal, the process comprises reacting an organohydrosilane with a vinylic compound in the presence of RhCl(di-tert-butylsulfide)$_2$ as a catalyst. Values for carbonyl by-product produced by this process range from about two to nine percent of weight of products formed by the process. The process taught by Dinh et al. is a preferred process for producing a mixture comprising a silyl ketene acetal and a carbonyl by-product for use in the present method.

SUMMARY OF INVENTION

The present invention is a method for separating silyl ketene acetals from carbonyl by-products having a terminal olefinic bond and a boiling point similar to that of the silyl ketene acetals. The method employs a platinum catalyst which specifically effects hydrosilation of the carbonyl by-product's terminal olefinic bond by an organohydrosilane. The platinum catalyst is the reaction product of hexachloroplatinic acid and sym-tetramethyldivinyldisiloxane. In a preferred method the silyl ketene acetal is separated from the hydrosilated carbonyl by-product by distillation.

DESCRIPTION OF INVENTION

The present invention is a method for purifying silyl ketene acetals. The method comprises:

(A) contacting a mixture comprising a silyl ketene acetal described by formula

$$H_3C-CR^1=C(OSiR_3)(OR^2) \qquad (1)$$

and a carbonyl by-product having a terminal olefinic bond and a boiling point similar to that of the silyl ketene acetal with an organohydrosilane described by formula

$$R_3SiH \qquad (2)$$

and a platinum catalyst comprising the reaction product of hexachloroplatinic acid and symtetramethyldivinyldisiloxane, and (B) separating the silyl ketene acetal from hydrosilated carbonyl by-product; where each R is a radical independently selected from a group consisting of alkyls comprising one to 20 carbon atoms, alkoxys comprising one to 20 carbon atoms, cycloalkyls comprising four to 20 carbon atoms, halogenated hydrocarbons comprising one to 20 carbon atoms, aryls, and aryloxys; each $R^1$ is independently selected from a group consisting of R and hydrogen; and $R^2$ is selected from a group consisting of alkyls comprising one to 20 carbon atoms, halogenated hydrocarbons comprising one to 20 carbon atoms, aryls, triorganosilyl radicals described by formula $—SiR_3$ where R is as previously described, and organooxy radicals of formula $—(CH_2)_nOR^3$ where n is an integer from one to ten and $R^3$ is selected from a group consisting of alkyls comprising one to 20 carbon atoms, cycloalkyls comprising four to 20 carbon atoms, halogenated hydrocarbons comprising one to 20 carbon atoms, aryls, and triorganosilyls described by formula $—SiR_3$ and R is as previously described.

The present invention is a method for purifying a mixture comprising a silyl ketene acetal and a carbonyl by-product having a terminal olefinic bond and a boiling point similar to that of the silyl ketene acetal (hereinafter referred to as "carbonyl by-product"). The method can be run in any standard reactor for contacting a mixture and a catalyst. The process can be run as a continuous process, semi-batch, or batch process. Preferred is when the method is run as a batch process in a stirred tank reactor.

The process for preparing the mixture useful in the present method is not critical and can be any of those processes known in the art for preparing silyl ketene acetals where carbonyl by-products are formed. Examples of such processes are presented in the Background Section herein. A preferred process for preparing the mixture is described in Dinh et al., Co-Pending U.S. Pat. application No. 07/912,433. Mixtures useful in the present method may be used without any preliminary purification, for example removal of residual catalyst.

The mixture comprises a silyl ketene acetal as described by formula (1). The silyl ketene acetal has substituent R, where each R is a radical independently selected from a group consisting of alkyls comprising one to 20 carbon atoms, alkoxys comprising one to 20 carbon atoms, cycloalkyls comprising four to 20 carbon atoms, halogenated hydrocarbons comprising one to 20 carbon atoms, aryls, and aryloxys. The radical R can be, for example, methyl, ethyl, propyl, isobutyl, tert-butyl, pentyl, methoxy, ethoxy, phenoxy, cyclopentyl, cyclohexyl, 3,3,3-trifluoropropyl, perfluoropropyl, chloromethyl, phenyl, tolyl, xylyl, and napththyl. Preferred is when R is an alkyl radical comprising one to six carbon atoms. Most preferred is when R is methyl.

The silyl ketene acetal has substituent $R^1$, where $R^1$ is selected from a group consisting of R and hydrogen and R is as previously described. Preferred is when $R^1$ is selected from a group consisting of hydrogen and methyl.

The silyl ketene acetal has substituent $R^2$, where $R^2$ is selected from a group consisting of alkyls comprising one to 20 carbon atoms, halogenated hydrocarbons comprising one to 20 carbon atoms, aryls, triorganosilyl radicals described by formula $-SiR_3$ where R is as previously described, and organooxy radicals described by formula $-(CH_2)_nOR^3$ where n is an integer from one to ten and $R^3$ is selected from a group consisting of alkyls comprising one to 20 carbon atoms, cycloalkyls comprising four to 20 carbon atoms, halogenated hydrocarbons comprising one to 20 carbon atoms, aryls, and triorganosilyls of formula $-SiR_3$ and R is as previously described. $R^2$ can be, for example, methyl, ethyl, phenyl, trimethylsilyl, trimethoxysilyl, dimethylphenylsilyl, and trimethylsilylethoxy. Preferred is when $R^2$ is selected from a group consisting of methyl, trimethylsilyl, and trimethysilylethoxy.

In addition to the silyl ketene acetal, the mixture comprises a carbonyl by-product. The carbonyl by-product must have a terminal olefinic bond. In addition, it is preferred that the carbonyl by-product have a boiling point similar to that of the silyl ketene acetal. By similar boiling point, it is meant that the boiling points of the carbonyl by-product and the silyl ketene acetal are close enough to each other to make separation by standard distillation methods difficult. The carbonyl by-products which may be separated out of the mixture by the present method are described by formula $H_2C=CR^1-CH(OSiR_3)(OR^2)$, where R, $R^1$, and $R^2$ are as previously described for the silyl ketene acetal. The amount of carbonyl by-product present in the mixture is not critical to the present method. Generally it is preferred that the carbonyl by-product comprise less than 50 weight percent of the mixture. More preferred is when the carbonyl by-product comprises about 1.0 to 25 weight percent of the mixture.

The mixture comprising the silyl ketene acetal and carbonyl by-product is contacted with an organohydrosilane described by formula (2). The organohydrosilane contains three independently selected substituents R, where R is as previously described. Those skilled in the art will recognize that the R substituents of the organohydrosilane can be different than the R substituents of the silyl ketene acetal and the carbonyl by-product. The preferred organohydrosilane is trimethylsilane.

The amount of organohydrosilane added to the method will depend upon the amount of carbonyl by-product present in the mixture. In general it is preferred that the organohydrosilane be added to the method at a concentration of about stoichiometric equivalence to about 20 mole percent stoichiometric excess in relation to the carbonyl by-product. Preferred is when the organohydrosilane is added to the method at a concentration of about one to five mole percent excess.

The present method uses a platinum catalyst comprising the reaction product of hexachloroplatinic acid and sym-tetramethyldivinyldisiloxane (herein after referred to as platinum catalyst). The reaction product may be used as a concentrate or may be diluted in a liquid dimethylvinylsiloxy terminated polydimethylsiloxane. The platinum catalyst is specific for the hydrosilation of the terminal olefinic bond of the carbonyl by-product and causes minimal hydrosilation of the silyl ketene acetal. The concentration of platinum catalyst useful in the present method can be varied within a wide range. In general a useful concentration of platinum catalyst is that which provides an initial concentration of platinum within a range of about 5 to 300 ppm platinum in the mixture. Preferred is when the platinum catalyst provides an initial concentration of platinum within a range of about 10 to 100 ppm platinum in the mixture.

In a preferred method, the platinum catalyst is added to the mixture comprising the silyl ketene acetal and the carbonyl by-product. The organohydrosilane is then added to the method at a controlled rate. By "controlled rate" it is meant that the organohydrosilane is added to the reactor at a rate to maintain the temperature of the mixture within the desired range. The rate of addition of the organohydrosilane will depend upon such factors as the size of the reactor, chemical formula of the carbonyl by-product, concentration of the carbonyl by-product, and the use of alternative temperature control means. It is preferred that the organohydrosilane be added as a gas and that the gas be delivered beneath the surface of the mixture containing the platinum catalyst.

The temperature at which the present method can be run is not critical and can be any temperature sufficient to allow hydrosilation of the carbonyl by-product without excessive hydrosilation of the silyl ketene acetal. In general a temperature within a range of about 20° C. to 100° C. is considered useful. A preferred temperature is within a range of about 40° C. to 70° C.

In the present method the silyl ketene acetal is separated from hydrosilated carbonyl by-product. The present method effects hydrosilation of the terminal olefinic bond of the carbonyl by-product thereby increasing the molecular weight of the carbonyl by-product. Therefore, the separation of the silyl ketene acetal from the hydrosilated carbonyl by-product can be effected by standard means for separating mixtures by molecular weight. A preferred method for separating the silyl ketene acetal from hydrosilated carbonyl by-product is distillation.

The following examples are provided to illustrate the present invention. There examples are not intended to limit the scope of the present claims.

Example 1. The ability of a platinum catalyst to selectively hydrosilate the terminal olefinic bond of a carbonyl by-product in the presence of a similar boiling silyl ketene acetal was evaluated. The process was conducted in a reactor comprising a 250 mL 3-neck flask equipped with a dry-ice condensor, a magnetic stirrer, and a thermometer. A mixture comprising the silyl ketene acetal $(CH_3)_2C=C(OMe)(OSiMe_3)$ (labelled SKA1), the carbonyl by-product $H_2C=C(CH_3)CH(OMe)(OSiMe_3)$ (labelled CA1) and other materials having a boiling point higher than the silyl ketene acetal (labelled High Boilers) was employed in the process.

The mixture was prepared by reacting trimethylsilane with methylmethacrylate in the presence of RhCl(di-tert-butylsulfide)$_2$ catalyst by a process similar to that described in Dinh et al., Co-Pending U.S. Pat. application No. 07/912,433. About 148 g of the crude mixture was added to the reactor and heated to about 55° C. Then 0.356 g of platinum catalyst ($90 \times 10^{-6}$ mole of platinum) was added to the process. The platinum catalyst was the reaction product of hexachloroplatinic acid and sym-tetramethyldivinyldisiloxane. Trimethylsilane was fed as a gas to the reactor below the surface of the liquid present in the reactor. The cumulative percentage of the stoichiometric amount of trimethylsilane added at the time of sampling is provided in Table 1 under the heading "%Me$_3$SiH," where stoichiometric equivalence is based upon the total moles of olefinic species present in the initial mixture. Samples of the liquid present in the reactor where taken at various times as described in Table 1. The samples were analyzed by gas chromotography (GC) using a mass spectrometer (MS) as a detector. The results are presented in Table 1 as area percent under the GC-MS trace for SKA1, CA1, and high boilers.

TABLE 1

| Platinum Catalyzed Hydrosilation of Carbonyl By-Product | | | | |
|---|---|---|---|---|
| | | GC-MS Area Percent | | |
| Time (h) | % Me$_3$SiH | SKA1 | CA1 | High Boilers |
| 0.0 | 0.0 | 75.0 | 9.6 | 1.1 |
| 1.5 | 10.0 | 75.0 | 0.8 | 14.0 |
| 2.5 | 15.0 | 75.2 | 0.1 | 14.6 |

The results presented in Table 1 demonstrate the ability of the platinum catalyst to selectively convert CA1 to a higher boiling specie.

Example 2. (Not within the scope of the present invention) For comparison purposes, the ability of RhCl$_3$.3H$_2$0 to selectively catalyze the hydrosilation of the terminal olefinic bond of a carbonyl by-product in the presence of a similar boiling silyl ketene acetal was evaluated. The process was conducted the same as described in Example 1, with the exception that 0.0188 g of RhCl$_3$.3H$_2$0 was substituted in the process for the platinum catalyst. The results are reported in Table 2, with all headings as previously described.

TABLE 2

| RhCl$_3$.3H$_2$O Catalyzed Hydrosilation of Carbonyl By-Product | | | | |
|---|---|---|---|---|
| | | GC-MS Area Percent | | |
| Time (h) | % Me$_3$SiH | SKA1 | CA1 | High Boilers |
| 0 | 0 | 75 | 9.6 | 1.1 |
| 1 | 10 | 75 | 7.9 | 3.1 |
| 8 | 20 | 74 | 7.5 | 4.0 |

These results demonstrate that RhCl$_2$.3H$_2$0 is a less effective catalyst than the platinum catalyst of Example 1 for the hydrosilation of carbonyl by-product to a higher boiling specie.

Example 3. The ability of a diluted platinum catalyst to selectively catalyze the terminal olefinic bond of a carbonyl by-product in the presence of a similar boiling silyl ketene acetal was evaluated. The process was conducted the same as described in Example 1, with the exception that the platinum catalyst was diluted in a liquid dimethylvinylsiloxy terminated polydimethylsiloxane in an amount sufficient to achieve a platinum content of 0.7 weight percent. About 0.465 g of the diluted platinum catalyst ($15.3 \times 10^{-6}$ mole platinum) was added to 134 g of the crude mixture comprising SKA1 and CA1. The results are presented in Table 3, with all headings as previously described.

TABLE 3

| Diluted Platinum Catalyzed Hydrosilation of Carbonyl By-Product | | | | |
|---|---|---|---|---|
| | | GC-MS Area Percent | | |
| Time (h) | % Me$_3$SiH | SKA1 | CA1 | High Boilers |
| 0 | 0 | 76.0 | 8.2 | 0.6 |
| 1 | 20 | 76.3 | 0.5 | 12.8 |

The results presented in Table 3, demonstrate the ability of the diluted platinum catalyst to selectively convert CA1 to a higher boiling specie.

Example 4. The ability of a platinum catalyst to selectively hydrosilate the terminal olefinic bond of a carbonyl by-product in the presence of a similar boiling silyl ketene acetal was evaluated. The process was conducted similar to that described in Example 1, with the exception that the mixture comprised the silyl ketene acetal $(CH_2)_2C=C\{OSi(CH_3)_3\}\{O(CH_2)_2OSi(CH_3)_3\}$ (labelled SKA2), the carbonyl by-product $H_2C=C(CH_3)CH\{OSi(CH_3)_3\}O\ \{(CH_2)_2OSi(CH_3)_3\}$ (labelled CA2), and other unidentified materials having a boiling point higher than that of the silyl ketene acetal (labelled High Boilers). The mixture was prepared by reacting trimethylsilane with trimethylsilylhydroxyethylmethacrylate in the presence of RhCl(di-tert-butylsulfide)$_2$ catalyst by a process similar to that described in Dinh et al., Co-Pending U.S. Pat. application No. 07/912,433. About 50.8 g of the crude mixture was added to the reactor, the temperature brought to about 60° C. and then 0.066 g of the platinum catalyst ($16.87 \times 10^{-6}$ moles of platinum) added to the reactor. Trimethylsilane was then fed to the reactor and the content of the reactor was sample at the times described in Table 4. Each sample was analyzed by GC-MS and the results are provided in Table 4. Unless otherwise described, the headings for Table 4 are as previously described for Table 1.

TABLE 4

| | Platinum Catalyzed Hydrosilation of Carbonyl By-Product | | | |
|---|---|---|---|---|
| | | GC-MS Area Percent | | |
| Time (h) | % Me$_3$SiH | SKA2 | CA2 | High Boilers |
| 0.0 | 0 | 75.5 | 7.4 | 1.5 |
| 1.5 | 10 | 77.2 | 2.3 | 8.8 |
| 2.5 | 20 | 77.0 | 0.5 | 9.8 |

The results presented in Table 4 demonstrate the ability of the platinum catalyst to selectively convert CA2 to a higher boiling specie.

Example 5. The ability of a platinum catalyst to selectively hydrosilate the terminal olefinic bond of a carbonyl by-product thereby facilitating separation from a silyl ketene acetal having a boiling point similar to the carbonyl by-product was evaluated. Except as provided below process conditions were similar to those described in Example 1. A crude mixture comprising SKA1, CA1, and high boilers was prepared by reacting trimethylsilane with methylmethacrylate in the presence of RhCl(di-tert-butylsulfide)$_2$ in a process similar to that described in Dinh et al., Co-Pending U.S. Pat. application No. 07/912,433. This crude mixture, containing the RhCl(di-tert-butylsulfide)$_2$, was reacted with trimethylsilane, in the presence of platinum catalyst providing a $20 \times 10^{-6}$ molar concentration of platinum. A sample of the reactor contents was taken at the times given in Table 5. Each sample was analyzed by GC-MS and the results are provided in Table 5. The headings for Table 5 are as previously described for Table 1.

TABLE 5

| | Platinum Catalyzed Hydrosilation of Carbonyl By-Product | | | |
|---|---|---|---|---|
| | | GC-MS Area Percent | | |
| Time (h) | % Me$_3$SiH | SKA1 | CA1 | High Boilers |
| 0 | 0 | 76.0 | 8.2 | 0.6 |
| 1 | 20 | 76.3 | 0.5 | 12.8 |

After one hour the reactor content was fractional distilled to recover the desired SKA1 product. A greater than 98% pure SKA1 with less than 0.1% CA1 content was recovered. These results demonstrate the ability of platinum catalyst to selectively facilitate hydrosilation of CA1 and facilitate CA1 separation from SKA1.

We claim:

1. A method for purifying silyl ketene acetals, the method comprising:
   (A) contacting a mixture comprising a silyl ketene acetal described by formula H$_3$C—CR$^1$=C(OSiR$_3$)(OR$^2$) 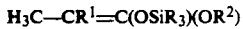

and a carbonyl by-product having a terminal olefinic bond and a boiling point similar to that of the silyl ketene acetal with an organohydrosilane described by formula R$_3$SiH 

and a platinum catalyst comprising the reaction product of hexachloroplatinic acid and sym-tetramethyldivinyldisiloxane, and
   (B) separating the silyl ketene acetal from hydrosilated carbonyl by-product;
   where each R is a radical independently selected from a group consisting of alkyls comprising one to 20 carbon atoms, alkoxys comprising one to 20 carbon atoms, cycloalkyls comprising four to 20 carbon atoms, halogenated hydrocarbons comprising one to 20 carbon atoms, aryls, and aryloxys; R$^1$ is selected from a group consisting of R and hydrogen; and R$^2$ is selected from a group consisting of alkyls comprising one to 20 carbon atoms, halogenated hydrocarbons comprising one to 20 carbon atoms, aryls, triorganosilyl radicals described by formula —SiR$_3$ where R is as previously described, and organooxy radicals of formula —(CH$_2$)$_n$OR$^3$ where n is an integer from one to ten and R$^3$ is selected from a group consisting of alkyls comprising one to 20 carbon atoms, cycloalkyls comprising four to 20 carbon atoms, halogenated hydrocarbons comprising one to 20 carbon atoms, aryls, and triorganosilyls described by formula —SiR$_3$ and R is as previously described.

2. A method according to claim 1, where the method is run as a batch process in a continuous stirred tank reactor.

3. A method according to claim 1, where R is methyl.

4. A method according to claim 1, where R$^1$ is selected from a group consisting of hydrogen and methyl.

5. A method according to claim 1, where R$^2$ is selected from a group consisting of methyl, trimethylsilyl, and trimethylsilylethoxy.

6. A method according to claim 1, where the carbonyl by-product comprises about 1.0 to 25 weight percent of the mixture.

7. A method according to claim 1, where the organohydrosilane is trimethylsilane.

8. A method according to claim 1, where the organohydrosilane is added to the method at a concentration of about one to five mole percent excess in relation to the carbonyl by-product.

9. A method according to claim 1, where the platinum catalyst provides an initial concentration of platinum within a range of about 10 to 100 ppm platinum in the mixture.

10. A method according to claim 1, where the platinum catalyst is added to the mixture and the organohydrosilane is delivered as a gas beneath the surface of the mixture containing the platinum catalyst.

11. A method according to claim 1, where the temperature of the mixture is within a range of about 40° C. to 70° C.

12. A method according to claim 1, where the silyl ketene acetal is separated from the hydrosilated carbonyl by-product by distillation.

13. A method according to claim 1, where R is methyl; R$^1$ is selected from a group consisting of hydrogen and methyl; R$^2$ is selected from a group consisting of methyl, trimethylsilyl, and trimethylsilylethoxy; the carbonyl by-product comprises about 1.0 to 25 weight percent of the mixture; the platinum catalyst provides an initial concentration of platinum within a range of about 10 to 100 ppm platinum in the mixture; and the temperature of the mixture is within a range of about 40° C. to 70° C.

14. A method according to claim 13, where the platinum catalyst is added to the mixture and the organohydrosilane is added beneath the surface of the mixture containing the platinum catalyst.

15. A method according to claim 14, where the organohydrosilane is trimethylsilane.

* * * * *